U S009486284B2

United States Patent
Depfenhart et al.

(10) Patent No.: US 9,486,284 B2
(45) Date of Patent: Nov. 8, 2016

(54) LASER THERAPY SYSTEM WITH UVA AND IR LASER LIGHT FOR DIRECTIONAL GENERATION OF A DERMAL COLLAGEN MATRIX

(75) Inventors: Markus Depfenhart, Hamburg (DE); Jörg Müller, Buchholz (DE)

(73) Assignee: TELESTO GMBH, Ulm (DE)

(*) Notice: Subject to any disclaimer, the term of this patent is extended or adjusted under 35 U.S.C. 154(b) by 462 days.

(21) Appl. No.: 13/552,711

(22) Filed: Jul. 19, 2012

(65) Prior Publication Data

US 2013/0023966 A1    Jan. 24, 2013

(30) Foreign Application Priority Data

Jul. 20, 2011    (DE) ........................ 10 2011 052 002

(51) Int. Cl.
| | | |
|---|---|---|
| *A61N 5/067* | (2006.01) | |
| *A61B 18/20* | (2006.01) | |
| *A61N 5/06* | (2006.01) | |
| *A61B 18/00* | (2006.01) | |

(52) U.S. Cl.
CPC ...... *A61B 18/203* (2013.01); *A61B 2018/0047* (2013.01); *A61B 2018/207* (2013.01); *A61N 5/062* (2013.01)

(58) Field of Classification Search
CPC .......... A61N 5/062; A81B 2018/0047; A81B 2018/207; A81B 2018/00452; A61B 18/203
USPC .................. 607/88–90; 606/4–6, 9
See application file for complete search history.

(56) References Cited

U.S. PATENT DOCUMENTS

| | | | |
|---|---|---|---|
| 4,930,504 A | | 6/1990 | Diamantopoulos et al. |
| 4,973,848 A | * | 11/1990 | Kolobanov et al. ....... 250/458.1 |
| 6,165,170 A | * | 12/2000 | Wynne et al. ................... 606/9 |
| 7,033,381 B1 | * | 4/2006 | Larsen ........................... 607/88 |
| 7,198,634 B2 | | 4/2007 | Harth et al. |
| 2003/0060810 A1 | * | 3/2003 | Syrowicz et al. ............... 606/9 |
| 2003/0175328 A1 | * | 9/2003 | Shefer et al. ................ 424/449 |
| 2005/0154381 A1 | * | 7/2005 | Altshuler et al. ................ 606/9 |
| 2005/0278002 A1 | * | 12/2005 | Eimerl et al. ................. 607/88 |
| 2006/0085053 A1 | * | 4/2006 | Anderson et al. ............. 607/94 |

(Continued)

FOREIGN PATENT DOCUMENTS

| | | |
|---|---|---|
| WO | 02053050 | 7/2002 |
| WO | 2008001284 | 1/2008 |
| WO | 2008089344 | 7/2008 |

*Primary Examiner* — Gary Jackson
*Assistant Examiner* — Boniface N Nganga
(74) *Attorney, Agent, or Firm* — Mark M. Friedman (57) ABSTRACT

The present invention refers to a Laser therapy system and a method for skin treatment, comprising:

a unit for dispensing a Photosensitizer containing agent;

a first light source which generates at least one first light with a first wavelength;

a second light source as a Laser light source which generates at least a second light with a second wavelength;

an optical system which is connected to the first and to the second light source, comprising an electromechanical displacement device with an optical deflection and focusing system such that the first and second light gets focused and a respective focus point can be controllably positioned in the skin; and     a control unit for controlling the electromechanical displacement device and the first and the second light source such that the respective light spot with a controlled energy and position in the skin is produced.

21 Claims, 8 Drawing Sheets

(56) References Cited

U.S. PATENT DOCUMENTS

| | | | |
|---|---|---|---|
| 2007/0038270 A1* | 2/2007 | Ferren et al. | 607/88 |
| 2007/0106284 A1 | 5/2007 | Siegel | |
| 2008/0039769 A1* | 2/2008 | Peyman | 604/20 |
| 2008/0039827 A1* | 2/2008 | Ferren et al. | 606/9 |
| 2008/0145326 A1* | 6/2008 | Ferren et al. | 424/63 |
| 2008/0208179 A1* | 8/2008 | Chan et al. | 606/9 |
| 2008/0262482 A1* | 10/2008 | Hantash et al. | 606/9 |
| 2009/0054953 A1* | 2/2009 | Whitehurst | 607/88 |
| 2009/0069741 A1 | 3/2009 | Altshyuler et al. | |
| 2009/0149842 A1* | 6/2009 | Muller et al. | 606/5 |
| 2010/0010482 A1* | 1/2010 | Neuberger | 606/10 |
| 2010/0049177 A1* | 2/2010 | Boone et al. | 606/9 |
| 2010/0057060 A1* | 3/2010 | Herekar | 606/4 |
| 2010/0144746 A1* | 6/2010 | Frullini | 514/251 |
| 2010/0168824 A1* | 7/2010 | Toriser | 607/90 |
| 2010/0185266 A1* | 7/2010 | Suzuki | 607/90 |
| 2011/0130748 A1* | 6/2011 | Kellogg et al. | 606/9 |
| 2011/0237999 A1* | 9/2011 | Muller et al. | 604/20 |
| 2011/0263920 A1* | 10/2011 | Bourke et al. | 600/1 |
| 2011/0270092 A1* | 11/2011 | Kang et al. | 600/476 |
| 2011/0282333 A1* | 11/2011 | Herekar et al. | 606/5 |
| 2012/0083772 A1* | 4/2012 | Rubinfeld et al. | 606/4 |
| 2012/0215155 A1* | 8/2012 | Muller et al. | 604/20 |
| 2012/0283621 A1* | 11/2012 | Muller | 604/20 |
| 2012/0310083 A1* | 12/2012 | Friedman et al. | 600/431 |
| 2013/0053699 A1* | 2/2013 | Wu et al. | 600/476 |
| 2013/0338626 A1* | 12/2013 | Ferren et al. | 604/501 |

* cited by examiner

LASER THERAPY SYSTEM WITH UVA AND IR LASER LIGHT FOR DIRECTIONAL GENERATION OF A DERMAL COLLAGEN MATRIX

FIELD OF THE INVENTION

The present invention refers to a Laser therapy system mainly comprising a first light source in the UVA range, a second Laser light source with a second wavelength range, an optical system and a control and navigation unit by means of which light can be precisely focused and positioned and applied in the papillary dermis or in the sclera or conjunctiva of the eye. Preferably, the Laser therapy system comprises an imaging unit, for instance based on optical coherence tomography, so as to allow manual or automatic, precise positioning of light spots in the area to be treated of the skin and thus a physiological and anatomically precise remodeling of the exoskeleton. In addition, the invention comprises a method for collagen remodeling of the skin by means of said Laser therapy system.

BACKGROUND OF THE INVENTION

Currently, a plurality of methods and Laser therapy systems for skin rejuvenation and scar treatment are known and available which are based, for example, on fractionated Laser ablation or mesotherapeutic collagen induction methods. For fractionated Laser ablation, devices such as Fraxel®, for instance, are known and in use. A denaturation of collagen and, consequently, a "shrinking" of the tissue can also be achieved by radio frequency, for instance by a Thermage® device. Such methods and devices are generally based on the application of injuries in the skin by means of a mechanical or a thermal therapy device, such as a Laser, in different shapes and depths depending on the device. Subsequent repair processes of the body then eventually lead, by degradation of the destroyed tissue and reconstitution of the tissue, to skin rejuvenation or simply to an epidermal and/or subepidermal scar which can also lead to a smoothing of the skin. This is to be distinguished from "mesotherapeutic" methods which also comprise, in the broadest sense, a percutaneous collagen induction therapy, also called "needling". Here, microbleedings in the stratum papillare of the skin are produced, for example by means of a needle roller, causing a release of blood corpuscles, mainly thrombocytes, in the dermis. From the thrombocytes, among others, growth factors, such as TGFβ3, VEGF, EGF, for example, are then released. They promote the degradation and regeneration of scars and the formation of directed collagen in the dermis, causing a regeneration or rejuvenation of the skin to a certain degree. These treatment methods also include a perioperative treatment with vitamin A and vitamin C containing creams for achieving high local levels of vitamin A and vitamin C which are important cofactors or coenzymes, respectively, for the formation of collagen and elastin in a target region of the skin for forming collagen and elastin.

All the above-mentioned methods and devices have in common that they are either mainly superficial or quite invasive and therefore prone to high risks and side-effects, with a satisfactory macroscopic result, but no anatomically reconstructing effect. With "needling", in addition to the painfulness of the treatment, the danger of infection, both for the therapist and the patient, is not to be underestimated. A cosmetic-aesthetic method wherein blood penetrates the surface of the skin is not to be seen uncritically in the age of HIV and hepatitis. Further, there is little possibility of standardization and thus quality assurance of such a method since parameters such as application force of the needle instrument and thus depth of needle application in the skin, a change in direction causing a grid effect, a matrix shift and thus, possibly, multiple perforations of the same skin area are dependent on the therapist and therefore not measurable or comparable.

WO 2008/089344 A2 (Neev) describes a device and a method of an IR Laser application for a dermal Laser application wherein several focused light beams with up to 10,000 focus points or light spots, respectively, can be generated and applied. Since the light beams are focused with a specific focal length, the light beam penetrates the skin with a first cross-sectional area and with a first light density and generates, in the respective focus point in the treatment area of the skin, a second light density much higher than the first one, which in the focus point is high enough to cause a light-induced reaction of the skin. Applications described comprise, for example, a stimulation or deadening of hair roots, treatment of acne, tattoos, changes of color, tanning, eye treatment including a generation of subcutaneous cavities. The latter entails degeneration and transformation processes in the skin and the formation of collagen fibers. A focal length and an energy of the respective light beam are selected such that the epidermis is not perforated. The use of optical coherence tomography (OCT) as an imaging method allows an observation of the skin structure, for instance with hair roots, blood vessels, matrix cells and papillae, also in a perspective view, so that this area can be targeted with the light spots. The device can also comprise a cooling element for the skin, which, however, will hardly be necessary.

WO 2008/001 284 A2 (Verhagen at al.) describes a Laser therapy system and a method for skin treatment in the depth of the skin which is based on Laser induced Breakdown (LIOB). By means of a camera and a monitor, wrinkles can be made visible for targeted Laser treatment in the depth of the skin.

WO 02/053 050 A1 (Altshuler et al.) describes a device and a method for a light-induced treatment in the depth of the skin, wherein the light source can be either a Laser light source or a non-coherent light source. A plurality of focused light beams are created simultaneously by an optical system comprising many lenses arranged in a network-like structure which lenses are integral or non-integral. Furthermore, the device comprises a cooling element for the skin which can be either a skin contact plate or the lens system itself.

From U.S. Pat. No. 7,198,634 B2, a Laser therapy system for skin treatment is known which has both an infrared light source and a light source with a violet or blue spectrum.

All current methods, Laser-based or otherwise, do not comply with an anatomically physiological reconfiguration or remodeling of the skin tissue.

SUMMARY OF THE INVENTION

Therefore, one object of the invention is the provision of a Laser therapy system which eliminates the disadvantages of the state of the art and allows an anatomically physiological reconfiguration of the skin tissue and in particular of the collagen and elastin matrix. Another object of the invention is not to perforate the skin above the area of treatment nor to damage said skin by said Laser therapy system.

These objects are achieved by a Laser therapy system or a method, respectively, for skin treatment in a volume-like treatment area in a depth of the skin according to the independent claims 1, 21 and 22, respectively.

Other advantageous embodiments of the invention are indicated in the dependent Claims.

With the Laser therapy system on which the invention is based, in a first step a collagen and elastin basic structure can be induced in the skin in accordance with its physiological texture and then, in a second step, further apposition of collagen and elastin can be induced. Thus, it is possible not only to induce the exoskeleton but also to regenerate it physiologically without any scars and without perforation of the epidermis.

Also, the method and the Laser therapy system can be used for closing wounds without any scars.

In addition, it is also conceivable to employ the method and the Laser therapy system not only for the skin but also for other tissues, for instance to connect them.

A preferred embodiment according to the present invention is presented in the following figures and in a detailed specification, but is not intended to limit the present invention.

DETAILED DESCRIPTION OF THE PREFERRED EMBODIMENT

Figure 1:
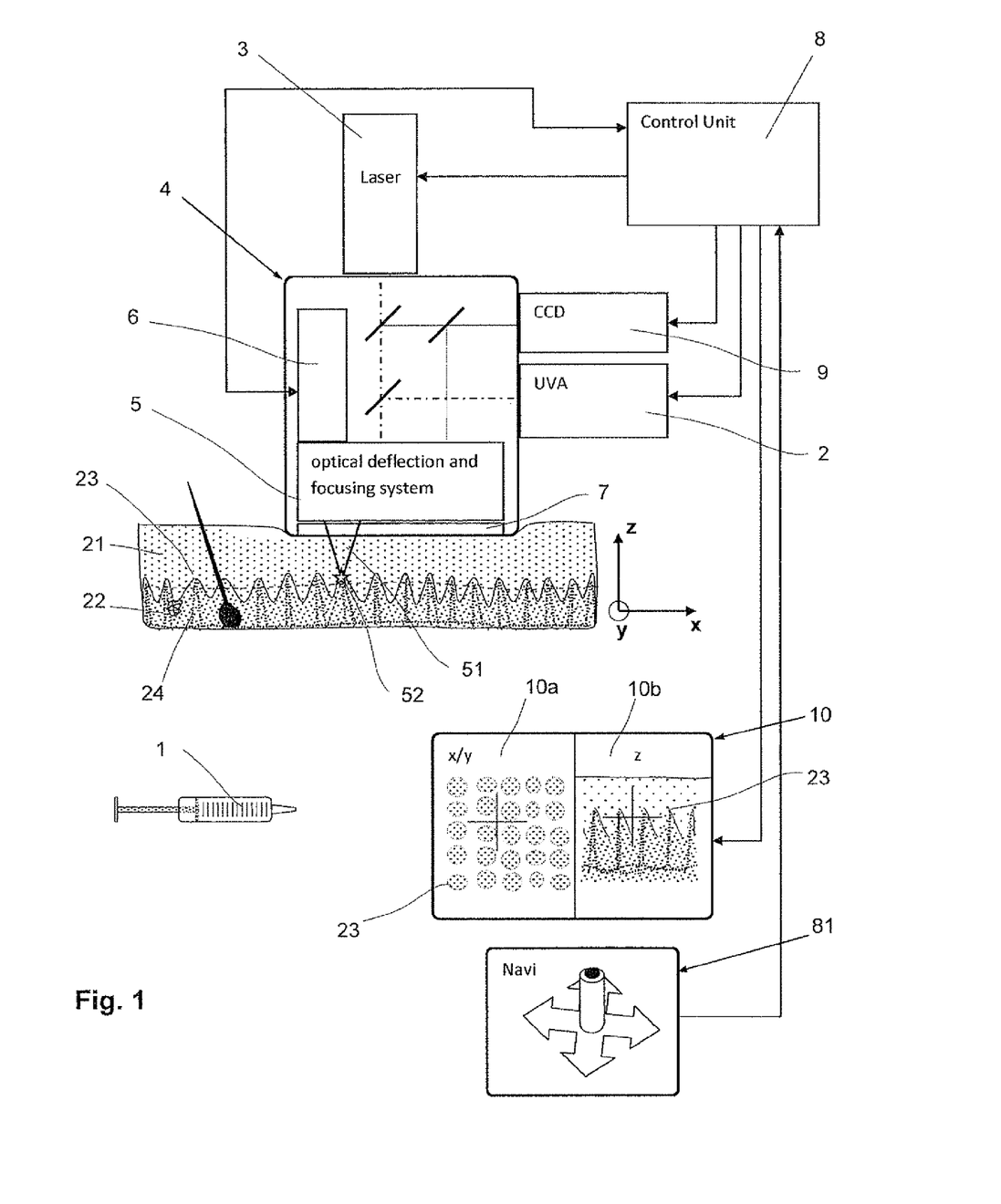
FIG. 1 shows a Laser therapy system as a block diagram with various components wherein a light beam emerges from or behind an adapter plate placed on an area of the skin of which the epidermis and the dermis are shown. In the lower half of the figure, a monitor receiving image data from a camera system for presenting the skin area, a navigation control device and a separate delivery unit for delivering an agent are shown.

FIG. 1 schematically represents a preferred Laser therapy system according to the invention, comprising a separate delivery unit 1 for delivering an agent containing a Photosensitizer, a first light source as a controllable UVA light source 2 with a first wavelength in the UVA range and a second light source 3 as a controllable Laser light source with a second wavelength and an optical system 4 to which the first 2 and the second light source 3 are connected. The light beams, also simply called light, of the first 2 and the second light source 3 are guided through the optical system 4 to an adapter plate 7 and passing through the adapter plate 7. Thus, the respective UVA light of the first light source and/or the second Laser light of the second light source 3 preferably exit the Laser therapy system behind the adapter plate 7 as a focused light 51 having a light spot in a focus point 52 behind the adapter plate 7. The focused light 51 preferably has the same focal length for the first and the second wavelength and a same position of the focus point 52 in an x/y/z coordinate system. For the employed wavelengths, the adapter plate 7 is made of a highly transparent material and preferably of sapphire glass which is also preferably very compatible with the skin. An additional skin adapter plate or foil between the adapter plate 7 and a patient's skin is conceivable as well. Preferably, the adapter plate 7 and the entire Laser therapy system are adapted for a patient's skin treatment. In FIG. 1, the adapter plate 7 is shown lying on a skin in lateral view, with the skin represented in a vertical cross-section in an x/z plane. A treatment area of the skin under the adapter plate 7 mainly consists of an epidermis 21 and a dermis 22 with protruding papillae 23 embedded therein and blood vessels 24 represented by doted lines.

The light of the UVA light source 2 and the second light source 3 are concentrated in the optical system 4 into a light beam, preferably, as shown, by means of semi-transparent mirrors, and then guided to an optical deflection and focusing system 5. The optical deflection and focusing system 5 consists preferably of a plurality of lenses and other optical elements, such as mirrors, prisms, light conductors and combinations thereof, which are necessary for light-beam expansion and focusing, for light deflection and/or for a controlled defined navigation of the focused light spot behind the adapter plate 7. The mirrors and semi-transparent mirrors shown in the optical system 4 can also be conceived as part of the optical deflection and focusing system 5. Some optical elements responsible for light deflection are preferably connected to actuators of an electromechanical adjusting device 6 so that via this adjusting device 6, the light beams can be deflected under electrical control so as to navigate the corresponding, resulting light spot or focus point 52. The actuators can be, for example, motors, stepper motors, piezoelectric actuators or magnetic actuators in combination with lever transmissions, driving gears and combinations thereof. It is also conceivable that the semi-transparent mirrors can be moved by actuators. Feedback signals from the actuators and pitch sensor signals and the like are preferably also taken into account and processed for keeping the light deflection precise.

A control unit 8 controls the actuators of the adjusting device 6 as well as the UVA light source 2 and the second light source 3 whose light intensities, adjustable pulse switching times and repetition rates are controllable, which means that the respective light source 2 or 3, respectively, emits defined light energies. A light-measuring signal for purposes of feedback and closed-loop control is preferably used as well.

As the UVA light source 2, preferably a switched Laser is used; however, it is also conceivable to use a non-coherent UVA light source 2 with a broader light beam than is the case with a Laser beam, which can accordingly be made adjustable and switchable by means of an aperture and a shutter. The first wavelength of the UVA light source 2 and the Photosensitizer containing agent are preferably matched with each other such that the light with the first wavelength is sufficiently absorbed by the Photosensitizer containing agent. Thus light spots with the first UVA wavelength, also simply called UVA light spots, applied to the skin treated with said agent induce a collagen and elastin cross-linking from one corner of the papillae 23 to the other. It should be mentioned that always only one specific head and tail region in the sense of the physiological lysyl oxidase reaction are connected. Such a connection is mediated by the Photosensitizer containing agent, such as, for example, riboflavin. The Photosensitizer containing agent is applied to the skin in a special pharmacological formulation which can penetrate the epidermis 21 well and thus reaches the papillary dermis 22 as its target structure. With the Photosensitizer containing agent, the necessary transmitted energy of the UVA Laser can be kept low and collateral damage caused by the UVA radiation, which is cytotoxical, can be avoided. Furthermore, the target region can be defined in this manner. Also, there is only so much energy applied with the UVA Laser as can be absorbed in this area by the Photosensitizer containing agent. Mixing the Photosensitizer containing agent with a fluorescent substance is conceivable as well. In this way, the penetration depth of the Photosensitizer containing agent in the target region can be controlled by means of a light source and/or a camera with a special color filter suitable for the fluorescence wavelength.

The UVA light has the first wavelength of preferably 340-450 nm. The UVA light beam which penetrates the skin behind the adapter plate 7 preferably has a first light intensity which is in the range of 100 μW-100 mW per focused light beam 51. In the focus point 52 of, the light intensity is diminished by the portion which was previously absorbed in the skin. The focus point preferably has a diameter of 5-10 μM, but it can also be preferably set at up to 100 μm. The focus depth behind the adapter plate 7 in the skin is preferably adjustable or controllable at a depth of 0.03-3 mm in the treated area. The focus depth is preferably also extendable by the thickness of a glass sheet or foil which can be inserted between the adapter plate 7 and the skin. The pulse duration is preferably 1 ms-1 s, but it can preferably also be set to be shorter or longer. With UVA light radiation, it is also conceivable in special cases to not generate the light beams 51 in a focused manner but to apply them onto the treated area of the skin in a planar manner.

As the second light source 3, preferably a switchable Laser is used. It is conceivable to expand the Laser beam and guide it through an aperture and through a shutter in order to regulate or control the light output additionally. The second wavelength, a second light intensity, a second pulse duration and a second pulse frequency or repetition rate, respectively, of the second light source 3 are preferably adapted for a good absorption of said light and for releasing energy in the focus point 52 so as to make the end arterioles permeable in as targeted a manner as possible and without greater collateral damage for blood cells. Preferably, the Laser parameters are set or triggered, respectively, in such a way that in the focus point 52 with the tissue, either a thermal, a photoablative or a plasma-induced reaction is produced. The second wavelength of the second Laser light preferably is 450-550 nm, particularly preferred 550-650 nm or 650-800 nm or 800-2000 nm in the IR range. The second wavelength is preferably selected and set such that the second wavelength is absorbed particularly well by hemoglobin and as little as possible by the tissue of the skin. The focused second is Laser light which enters the skin behind the adapter plate 7 preferably has a first cross-sectional area of 1-30 mm$^2$, which, however, can also be larger. The second light intensity preferably corresponds to 1 mW-100 W per focused light beam 51. In the focus point 52 or the light spot, respectively, the light intensity is diminished by the portion which was previously absorbed into the skin. The focus point preferably has a diameter of 10-100 μm. The focus depth behind the adapter plate 7 in the skin preferably lies within a range of 0.03-3 mm or larger and is adjustable or controllable. The pulse duration preferably is 10 ps-100 μs, but it can also be set to be shorter or longer.

Preferably, a navigation control device 81, formed e.g. as a joystick with corresponding control knobs or as a track bail, is connected to the control unit 8. In this manner, the position of the focus point 52 can preferably be defined precisely in the treated area of the skin in the x, y and z directions. Alternative and/or additional possibilities of input or control, respectively, e.g. by a touch screen monitor, voice recognition or image recognition of gestures or facial expressions, are possible as well.

Preferably, the Laser therapy system also comprises a camera system 9 and a monitor by means of which a physician in charge can visualize the skin to be treated and the light spot positions in the area to be treated, where the respective light spots of the first UVA light and/or the second Laser light are to be produced or guided to. In FIG. 1, for instance, on the monitor 10 on the left side of the image, a first image 10*a* is shown which indicates the area to be treated as a horizontal cross-section on an x/y plane, edges of the papillae 23 and a reticule indicating the position of a light spot to be produced. At the same time, on the right side of the monitor 10, a second image 10*b* of the vertical section on an x/z plane of the area of the skin to be treated is shown with the reticule indicating the x/z position of the light spot to be produced. A three-dimensional representation of the area to be treated or a magnification of the same are conceivable as well and can preferably be selected by the physician in charge.

The camera system 9 is preferably kept in the same optical path as the UVA and the second Laser light guided through the adapter plate 7. During this process, preferably an OCT-based imaging system is employed by means of which the area of the skin to be treated can be represented three-dimensionally and so in depth as well. Preferably, light with an imaging wavelength between 340 nm and 550 nm is used in this process. In picture recording and processing, however, it is also conceivable that, in a manner similar to digital subtraction angiography, two camera images with different parameters are captured and processed together in such a way that a desired structure of tissue and vessels can be contrasted. In case of said camera system 9, preferably different imaging wavelengths are used for irradiating the skin, wherein a first camera image being taken at a first imaging wavelength and a second camera image at a second imaging wavelength. Subsequently, the first and the second camera image are processed such that all structures of the area of the skin to be treated are largely eliminated and substantially only the papillae 23 of the stratum papillare and the blood vessels remain visible. Preferably, collagen and elastin fibers can also be selectably highlighted in this manner. Preferably, also the UVA light source 2 is used as one of the illumination sources. Preferably, the light spots produced are represented as small light dots on the monitor 10. Preferably, also the sites already treated are marked on the monitor so that the physician can easily see where treatment still has to take place; this applies to treatment with the first UVA wavelength as well as for the second wavelength of the Laser light. As an alternative to the OCT-based system, also an imaging system based on a fluorescence microscopy or a fluorescence tomography can be employed in which a fluorescence is induced either by injected or by topically applied fluorescent coloring and stimulation by light or Laser and in which this stimulation can be evaluated. Subsequent image processing can be the same as described above.

Preferably, the imaging system, comprising the camera system 9, the monitor 10 and a microprocessor unit which can also be part of the control system, is also used for pattern recognition. The pattern recognition is such that preferably the region of the papillary dermis 22 of the area to be treated is recognized so that the papillae 23 and the area between them where the UVA light spots are to be placed are recognized. The combination of the x/y/z coordinates of the UVA light spots results in a UVA light spot matrix as a first light spot matrix. By recognition of the papillae 23 and the end arterioles within them, the pattern recognition preferably also determines the x/y/z coordinate points, where second light spots of the second Laser light are to be placed, in an automated manner. The combination of the x/y/z coordinates of the second light spots, results in a second light spot matrix. Preferably, the UVA and/or the second light spots are generated in an automatic or semi-automatic manner by the control unit 8. In semi-automatic generation of the respective light spots, preferably one light spot after the other is marked on the monitor 10 and approved by the physician, or sequences with a specific number of light spots are marked on the monitor 10, approved by the physician and executed then automatically. Another preferred pattern recognition recognizes a shifting of the adapter plate 7 on the skin and transforms the x/y/z coordinates of the respective light spots to be generated, which have already been determined locally, to the current area to be treated under the adapter plate 7 so that the respective light spots are produced at the same places that were determined previously. Preferably, the treated and untreated areas of the stratum papillare are recognized so that with semi-automatic or automatic generation of the respective light spots, preferably only the areas which have not yet been treated are irradiated. Preferably, the pattern recognition also recognizes the correct depth z of the target region automatically, so as to set or preset the focus points 52 to the correct depth z by means of the control unit 8 so that in this case, the physician only has to give his approval.

Figure 2:
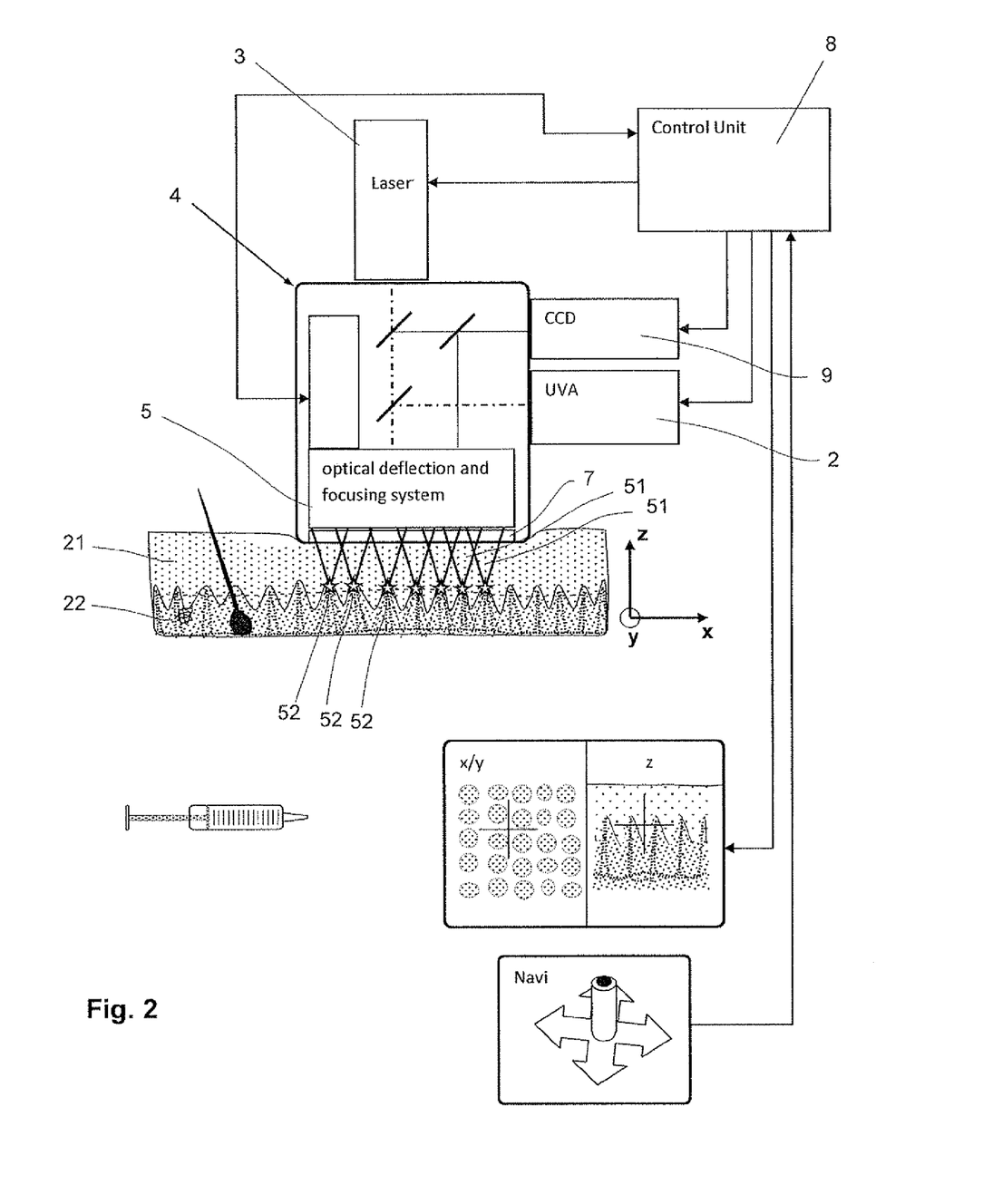
FIG. 2 shows a Laser therapy system as a block diagram with the components shown as in FIG. 1, with a plurality of light beams emerging simultaneously behind the adapter plate.

FIG. 2 schematically shows a similar structure of the Laser therapy system as FIG. 1; this embodiment, however, can generate a plurality of focused respective light spots or focus points 52, respectively, which are shown as stars, in a simultaneous, a sequential and in an automatic or semi-automatic manner. Semi-automatic means here that after the x/y/z coordinates of all respective light spots in the area of the skin to be treated under the adapter plate 7 have been determined as the respective light spot matrix by preferred pattern recognition and the physician has approved them for light spot application, the control unit 8 quickly applies one or more simultaneous respective light spots or a sequence of light spots. This goes for the respective light spot matrix both of the UVA wavelength and the second wavelength. For this purpose, the optical system 4, the optical deflection and focusing system 5 and the actuators of the adjusting device 6 are preferably constructed in such a manner that e.g. fast Piezo-actuators and optical elements with as little mass as possible are employed so as to allow as fast, precise and noiseless adjustments as possible. It is also conceivable to perform mechanical counter-movements of masses in the Laser therapy system in order to reduce vibrations, noises and wear and to increase precision therewith. Also, the adjusting movements are preferably not controlled causing abrupt but rather continuously rising or falling adjustment accelerations, so as to achieve a short settling time of the optical deflection and focusing system 5 in an optimum manner.

Preferably, the light spots of the respective light spot matrix, which, again for clarification, are not equidistant but physiologically meaningfully spaced from each other, are first applied in only one depth z in the area of the skin to be treated, with a first simultaneous generation of light spots or in a first sequence, so that for a next level or depth z of treatment, the physician would have to approve a subsequent generation of respective light spots or a next sequence of light spots. Alternatively, all respective light spots of the volume-like respective light spot matrix can be semi-automatically generated sequentially or simultaneously. In this process it is possible, for example, to set a maximum number of applied light spots after approval by the physician. Preferably for each respective wavelength the untreated areas are distinguished from the treated areas of the skin, and the untreated areas are further treated with respective light spots accordingly.

In alternative to the sequential, individual controlling of each x/y/z coordinate of the respective light spot, the optical system 4 or the UVA light source 2 and/or the second light source 3 can generate several light beams as a beam matrix which can be applied simultaneously as the focused light beams 51. Individual beams or individual focused light beams 51 can also be preferably blocked or not actuated if for physiological reasons, no light spot is to be produced in the respective focus point 52. It is conceivable for the optical system 4 to contain a multifocal lens as it has been described by Altshuler (WO 02/053 050 A1). Preferably, however, the optical system 4 comprises several individual lenses controllable in their positions, i.e. not having any constant and predefined distance from each other, but able to be actuated individually by several assigned actuators or adjustment devices in such a way that they are aligned in their respective adjustment area with the respective focus point 52 with one of the specific light spots of the light spot matrix. In this way, on the one hand, the treatment time can be substantially shortened, and, on the other hand, other than with Altshuler (WO 02/053 050 A1), where the light spots have predefined distances from each other which cannot be altered, the light spots can be positioned in a targeted and precise manner which is individually adapted to the tissue. Since in case of simultaneous application of the light spots according to the beam matrix, there are minimum distances of the light spots or beams to each other which are due to the component diameters of the LEDs, diode Lasers and/or the lenses or due to other components or mounting devices, preferably, after application of a first light spot generation, the optical system 4 and/or the first and the second light source 2 and 3, respectively, are displaced or adjusted such that the respective next light spots of the light spot matrix are covered by the next light spot generation. This process is repeated until the entire light spot matrix in the treatment area is covered. In case of a beam matrix consisting of, for example, 10×10 light spots, the treatment time can also be reduced by up to factor 100. It is also possible for the Laser therapy system to have adjustable light sources instead of an adjustable, multifocal lens system, with a plurality of individual light sources in the UVA and/or the second wavelength range being arranged next to each other in grid or matrix form and adjustable.

Preferably, above all, simultaneously or semi-automatically sequentially, several focused light beams 51 are generated with the first UVA wavelength as the first light spot matrix. Alternatively, the UVA light source 2 can be structured, for instance, as a diode Laser or LED matrix which creates the light beams, which can be focused or non-focused and can preferably be positioned individually for each light spot in the adjustment area, simultaneously in discrete spacing from each other.

For the second Laser light with the second wavelength, the same applies as for the UVA light. Here as well, preferably a second light spot matrix for the second Laser light with a corresponding number of parallel focused light beams 51 or focus points 52, respectively, can be generated and applied. In this case, however, precise positioning of the second light spots is of greater importance than with the UVA light, so that preferably a sequential triggering of each individual light spot is performed for the second Laser light.

Figure 3:
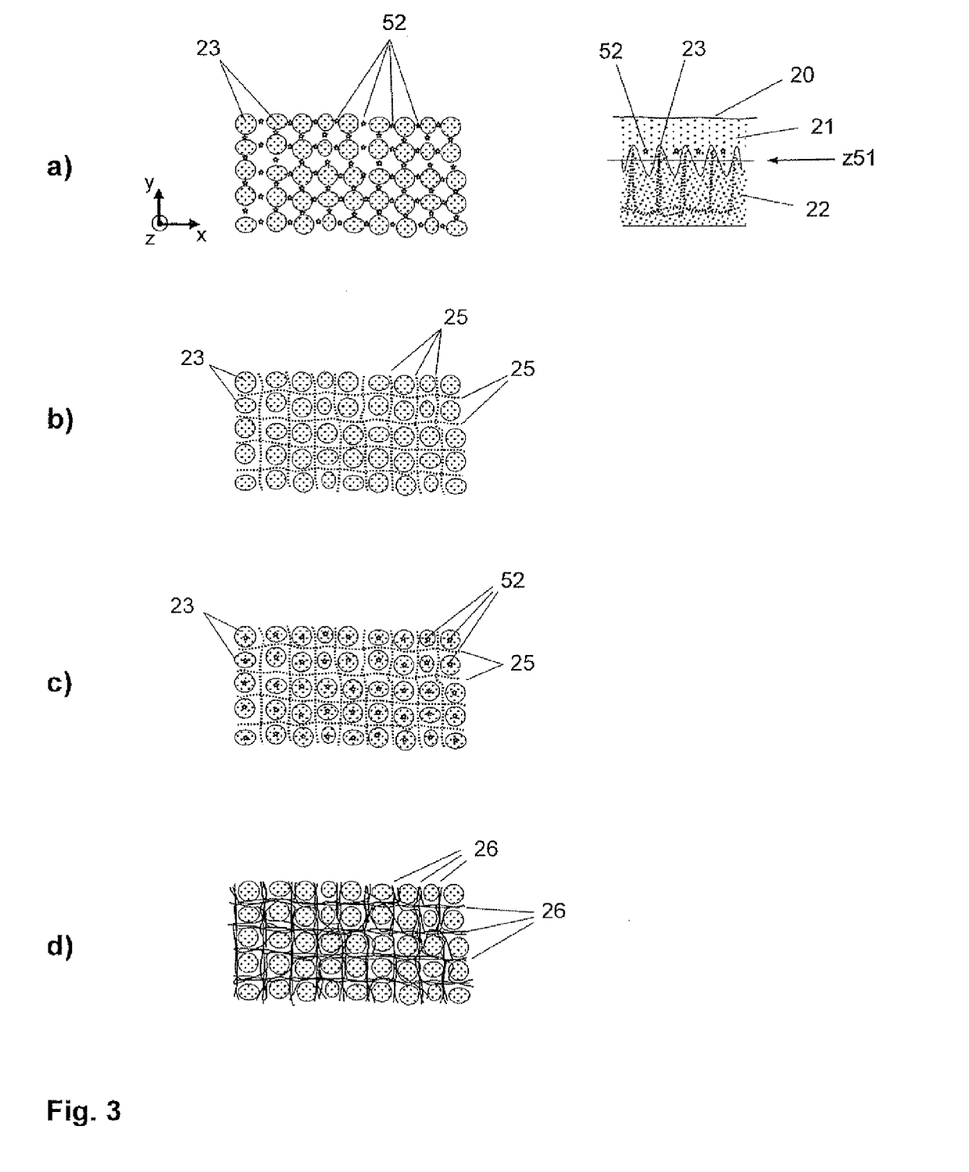
FIG. 3a shows in the left upper part, in top view, a schematized cross-section of a papillary dermis in a depth of the skin, parallel to the skin surface on an x/y plane, wherein substantially the edges of the papillae are shown in the cross-sectional plane. The stars shown between the edges of the papillae represent applied light spots in the UVA spectral range. The right side of the figure shows a schematized vertical cross-section of the skin indicating the height distribution and structure of the papillae with blood vessels. The stars shown there represent light spots.
FIG. 3b shows in top view the schematized cross-section of the same skin area as in FIG. 3a, but with a grid-like collagen and elastin basic structure created as a cross-linked net as a consequence of irradiation with UVA light spots, where the skin area was previously treated with the agent.
FIG. 3c shows in top view the schematized cross-section of the same skin area as FIG. 3b, but with a star-shaped representation of second light spots positioned on the papilla tips.
FIG. 3d shows in top view the schematized cross-section of the same skin area as FIG. 3c, but with additional collagen in apposition along the collagen and elastin basic structure which forms the pattern.

FIG. 3a shows, in top view, a schematized cross-section of a papillary dermis 22 in the depth of the skin, with the corresponding papillae 23 which are visible from the top as rounded rims. Between the papillae 23, focus points 52 are shown as star-shaped light spots at the places where they are supposed to be generated in the UVA wavelength and where they are finally generated. To the right thereof, the vertical cross-section of the area of the skin is shown which is also represented in top view at the left side of the image. Between the undulating papillae 23 shown in the vertical cross-section, the focus points 52 are also represented as star-shaped light spots.

FIG. 3b shows, in top view, the same schematized cross-section of the skin with the corresponding papillae 23 as FIG. 3a; here, however, application of the UVA light spots has resulted in an initial grid-shaped collagen and elastin basic structure 25 in the form of an initial collagen and elastin matrix between and around the papillae, formed by cross-linking, which matrix is represented by doted lines. It indicates directions and a network structure for fibroblasts which are the collagen forming cells for an addition and extension of an additional collagen 26 along the collagen and elastin basic structure 25.

FIG. 3c shows, in top view, the same schematized cross-section of the skin with the corresponding papillae 23 and the initial collagen and elastin basic structure 25 as shown in FIG. 3b; however, in addition the second focus points 52 of the second light source 3 are shown as stars. The second light spots are positioned as close as possible to the end arterioles of the corresponding papillae 23 so as to allow as much energy of the second light spot as possible to be absorbed by the end arterioles. The intensity and pulse duration of the second light spots is adapted to the depth of the light spots and the absorption of the previous skin layers and to the necessity that the desired amount of energy reaches the end arterioles. The Laser therapy system is preferably designed in such a way that the second Laser light, the second wavelength, the second pulse duration and the second intensity can be adapted or controlled in such a way that it is possible to choose between a thermal, a photoablative and a plasma-induced reaction of the skin tissue. The object is to be able to set or control said parameters in such a way that the end arterioles become permeable for the blood cells, and preferably for thrombocytes, for a sufficiently long time and preferably for up to 20-50 seconds. In this way, chemotaxis is stimulated; fibroblasts immigrate; and growth factors are released e.g. from the thrombocytes. The growth factors lead to the induction of the production of further collagen. The main determining growth factors are: TGF β3, VEGF, EGF, PDGF.

FIG. 3d shows, in top view, the same schematized cross-section of the skin with the respective papillae 23 and the initial collagen and elastin basic structure 25 as FIG. 3c; but with additional collagen 26 built up and attached by fibroblasts along the initial collagen and elastin basic structure 25 and around the papillae 23. The fibroblasts use the weak collagen and elastin basic structure 25 as a directional structure and migrate along the same, comparable to a spider in a web which repairs or enforces its web. With a treatment shown in FIG. 3c, which corresponds e.g. to a Laser needling, a process for complete regeneration of the skin's collagen structure, and consequently for complete remodeling of an adolescent exoskeleton, takes between 3 and 6 months.

Figure 4:
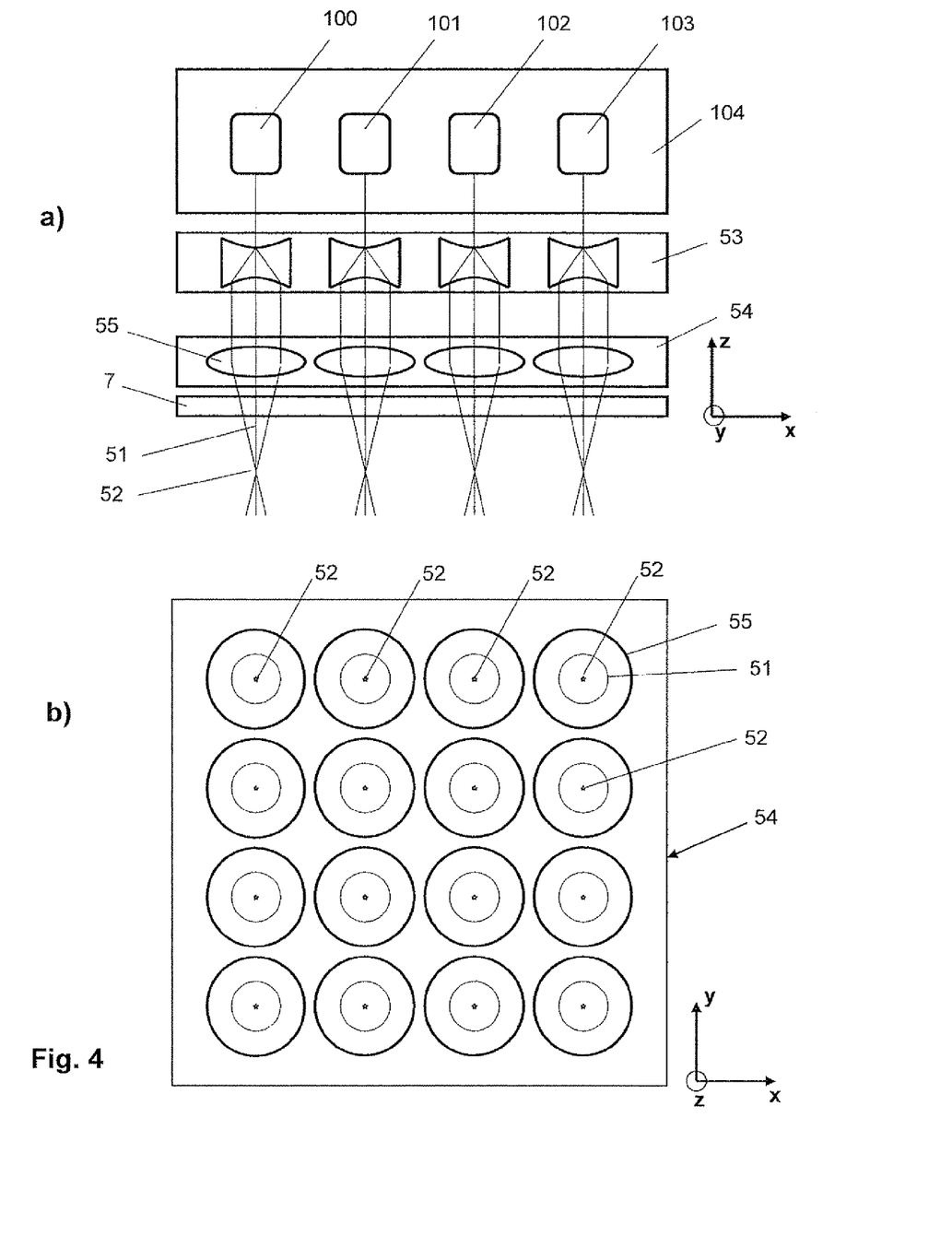
FIG. 4a schematically shows, in lateral view, a light source unit with various discrete light sources, a first lens system for light beam expansion, a second lens system for light beam focusing and an adapter plate with a corresponding light beam course.
FIG. 4b schematically shows in top view the second lens system of FIG. 4a with 16 lenses for light-beam focusing contained therein, with the thin lines within the lenses representing the beam diameter in passing through the lenses and the stars in their centers representing the focused light spots.
FIG. 4c shows in top view another schematized cross-section of the papillary dermis, represented larger than in FIG. 3a. Superimposed over it or in it, respectively, is a matrix of adjacent focus points (X1/Y1) to (X5/Y4) represented as stars whose position is hardware-dependent and each of which can be activated by the control unit as a light spot.

FIG. 4a schematically shows, in lateral view, a preferred device of a light-source unit 104 with four integrated light sources in the positions 100-103, which forwards their light beams to a first lens system 53 and couples them to it. The first lens system 53 preferably contains biconcave lenses which widen the entering light beams and create accordingly widened respective light beams. A second lens system 54 is coupled to the first lens system 53, which lens system 54 takes up the widened light beams, guides them each through a lens 55 and focuses them with a specific focus point 52 so that from the widened light beams, focused light beams 51 with one focus points 52 each are produced behind the lenses. To the light output of the second lens system 54, the adapter plate 7 is coupled at a defined distance so that the focused light beams 51 exit behind the adapter plate 7 in a defined manner. If the second lens system is displaced in depth z, the focus points 52 are displaced to the same extent.

In this way, the depth z of the focus points 52 can easily be adjusted or controlled behind or below the adapter plate 7, respectively.

In the example in FIG. 4a, four Laser diodes are conceivable in positions 100-103, two of which preferably two emit light in the UVA range and two emit light with the second wavelength. For instance, UVA light diodes are employed in positions 100 and 102 and Laser diodes for the second Laser light are employed in positions 101 and 103.

FIG. 4b schematically shows in top view from the first lens system 53, the second lens system 54 of the preferred device of FIG. 5a. The arrangement shows four times four lenses in the x and y directions, wherein in each lens 55, the emitted focused light beams 51 are shown as fine lines and the generated points of focus 52 in star shape. In this case, the generated points of focus 52 behind the second lens system 54 represent the respective beam matrix of the system.

Figure 4C:
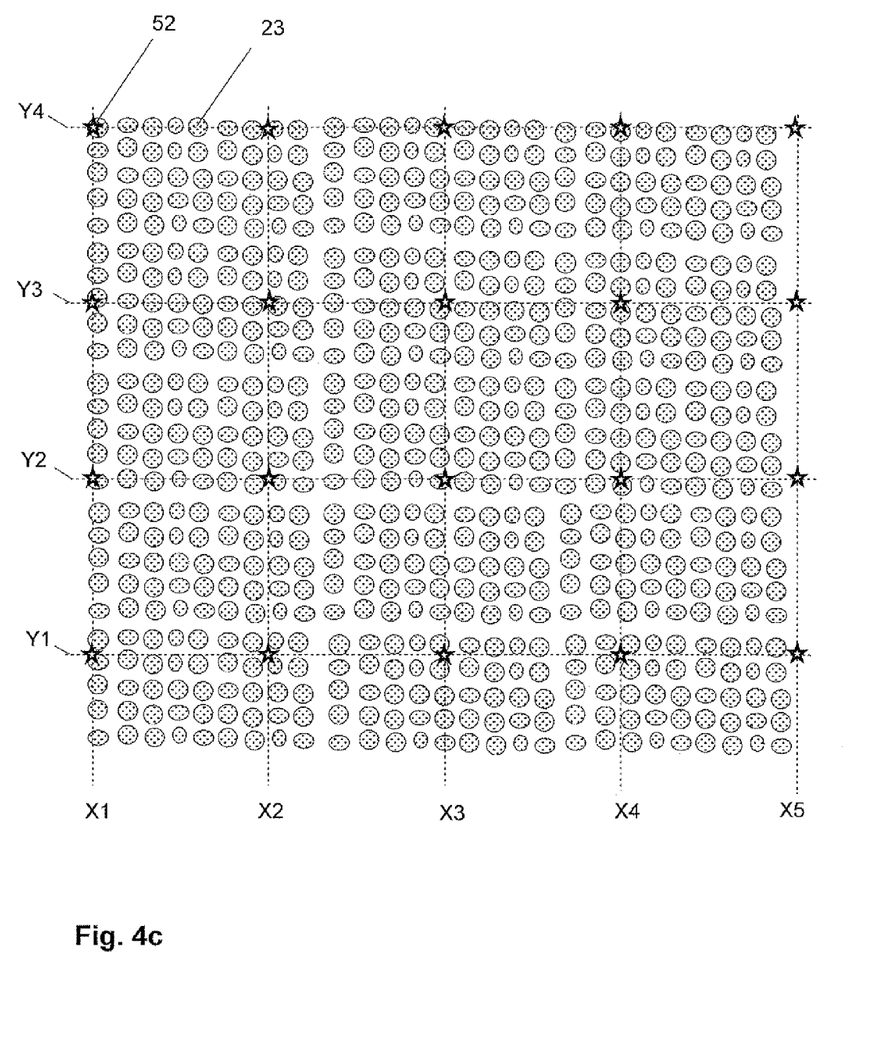

FIG. 4c schematically shows a section of a larger treatment area of the skin with its suggested dermal papillae 23. The focus points 52 of a different beam matrix are shown overlaid on it, e.g. indicated by stars, with a coordinate (X1/Y1)-(X5/Y4) being assigned to each light spot of the beam matrix. This example is used to explain that with a definite and equidistant beam matrix according to Altshuler (WO 02/053 050 A1), not all the produced beams are in the physiologically correct position, but preferably only part of the beam, namely those beams which are positioned correctly by accident. In the present example, assuming that a specific capture range with tolerance is defined in which, for instance, the second light spots are still allowed to be generated, all beams with the exception of those beams at the coordinates (X2/Y1)-(X5/Y1), (X2/Y2), (X2/Y3), (X5/Y2)-(X5/Y4) would be activated as light spots. In case of a preferred device where the individual beams can be displaced by +/−10% of a basic distance, each one of the beams can be positioned correctly in physiological terms and create a light spot before the entire displacement of the device.

Figure 5:
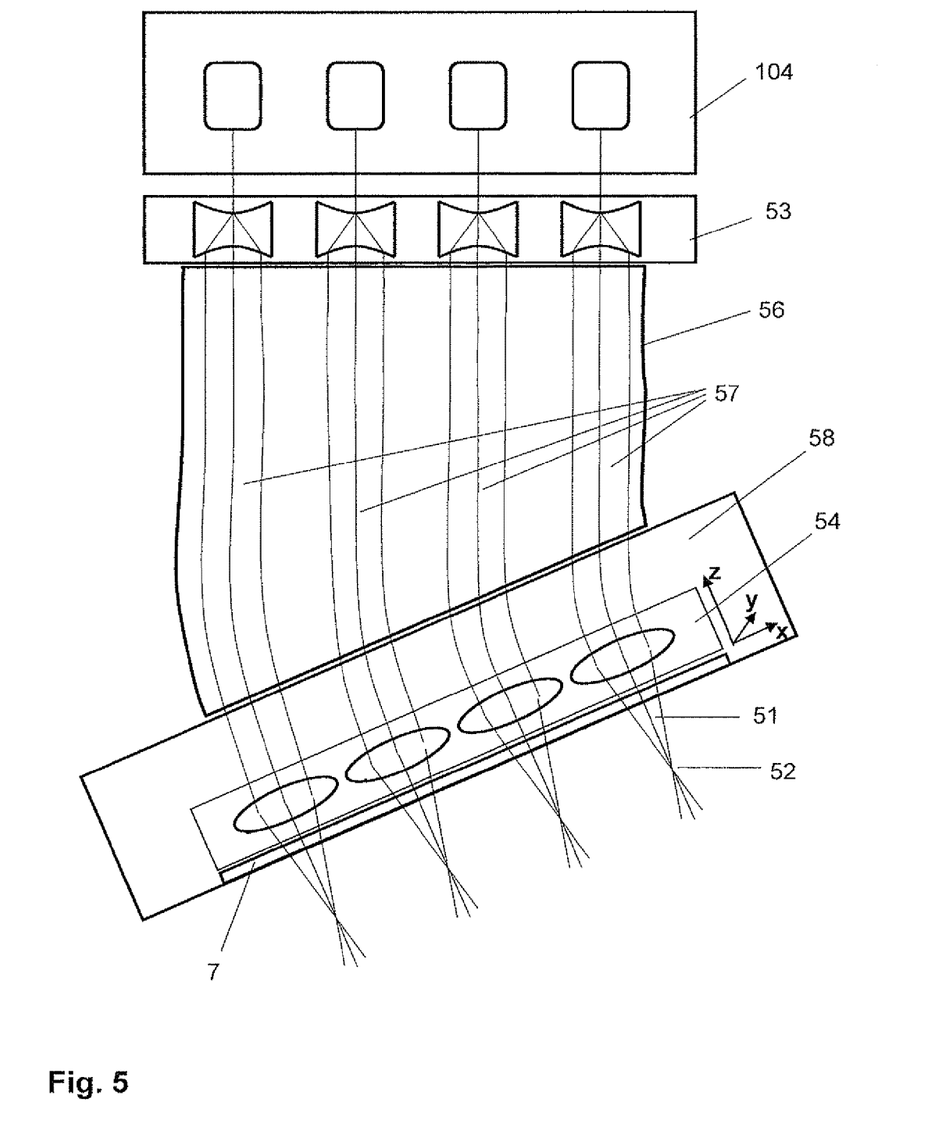
FIG. 5 schematically shows in lateral view the light source unit, the first lens system, an optical guide with light fiber beams, a light adapter head with the second lens system and the adapter plate.

FIG. 5 shows a preferred device similar to the one in FIG. 4a, comprising the light source unit 104 with its four integrated light sources and the first lens system 53 coupled to it, from which the expanded light beams exit and are now coupled to a light conductor 56. The light conductor 56 guides the expanded light beams by means of optical fiber beams 57 contained in it and, as a flexible light conductor 56, guides the expanded light beams to a light adapter 58 which forwards the expanded light beams further. The light adapter 58 comprises the focusing second lens system 54 and guides the entering light beams to the adapter plate 7 through the second lens system 54. The focused light beams 51 which were generated by the second lens system 54 exit behind the adapter plate 7 of the light adapter 58 placed on the skin in such a way that the focused light beams 51 and the focus points 52 exit the light adapter 58 spatially defined and thus can be positioned or guided, respectively, in the treatment region of the skin. The main advantage of this system is the separation of the Laser therapy system into a heavy, large part and a relatively small, flexible and easy-to-handle part which is placed on the skin, fixed into place there for a short time for the purpose of treatment and then shifted to a next treatment site. By adjusting the depth z of the second lens system 54 e.g. in the light adapter 58, the focus point 52 can be positioned or adjusted behind the adapter plate 7.

Such an arrangement of a separation of the first, heavy and large, part of the Laser therapy system from the relatively small, flexible and easy-to-handle part placed on the skin is also conceivable and preferred for all other devices according to the invention described herein, such as those from FIG. 1 or FIG. 2, and is only omitted for the sake of clarity. A different preferred light conductor 56 comprises mirror systems instead of light fiber beams 57.

Figure 6A:
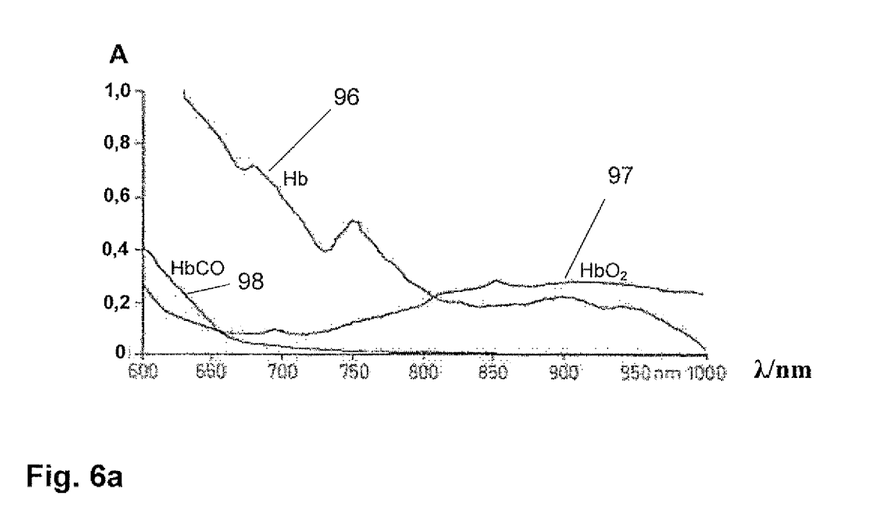
FIG. 6a shows a diagram with characteristic spectral absorption curves of oxygenated and non-oxygenated hemoglobin in dependence on the wavelength. The specific absorption coefficient is shown on the ordinate. Source: J. Eichmeier: Medizinische Elektronik, 2nd edition, 1991, Springer Verlag.

In FIG. 6a, the specific absorption coefficient is shown over the illumination wavelength of oxygenated blood 97 and of deoxygenated blood 96. Additionally, the specific absorption coefficient of blood 98 enriched with carbon monoxide is shown. The table is taken from J. Eichmeier: *Medizinische Elektronik*, $2^{nd}$ ed. The diagram is to illustrate that with different illumination wavelengths, different substances and tissue parts can be detected with more or less specific contrast. For detection of the end arterioles in the papillae 23, preferably a first image is taken with a first illumination wavelength of 800 nm in the isosbestic point a second image with a different second illumination wavelength of e.g. 650-750 nm, and both are processed together. For image processing, preferably logarithmic processing of the intensities of the first and the second image with subsequent subtraction of one from the other is performed. Other edge enhancement algorithms show end arterioles in particular contrast in relation to the question where e. g. the papillae 23 are located in the treatment area and where the second light spots are supposed to be set. Alternatively, illumination can also take place with white light or with both illumination wavelengths at the same time if an image is taken with a color CCD camera and then one image is obtained from the red portion, one image from the green portion and one image from the blue portion of the colored image and all are processed together.

Figure 6B:
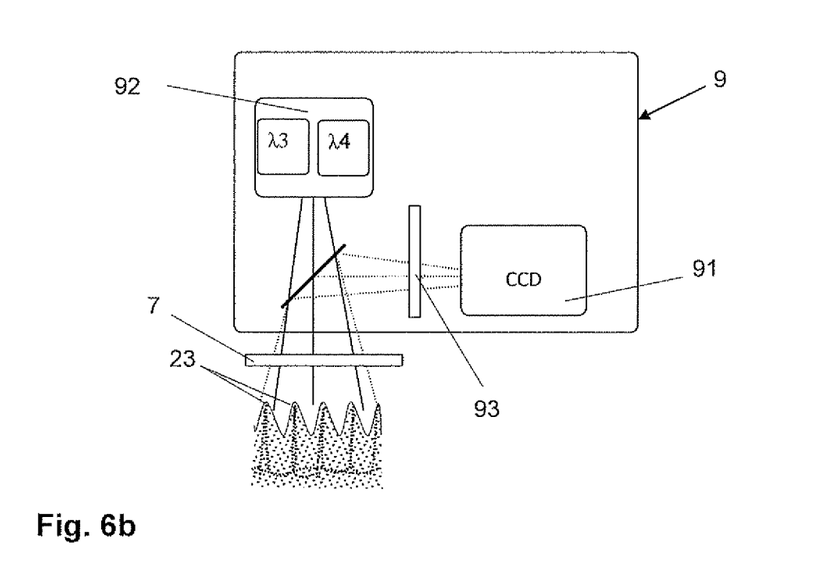
FIG. 6b shows a schematic structure and an arrangement of a camera system coupled to the skin via the adapter plate, with the skin schematically shown as a vertical dermal section.
Figure 6C:
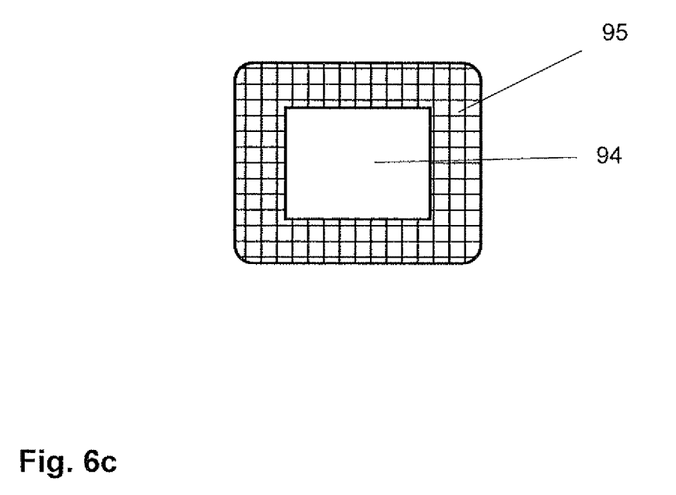
FIG. 6c schematically shows, in top view, a detection array and an illumination array of the camera system which is arranged around it.

FIG. 6b schematically shows a camera system 9 preferably comprising a camera unit 91, e. g. embodied as a CCD sensor, one or more optical filters 93, a semitransparent mirror and an illumination source 92. The optical path of the illumination source 92 is directed to the skin by means of the semitransparent mirror through the adapter plate 7, is reflected there on the surface and in depth, with the reflected beams also passing through the adapter plate 7 and again being reflected to the camera unit by the semitransparent mirror. The illumination source 92 preferably comprises at least two separate illumination sources or one common illumination source emitting at least the first illumination wavelength and the second illumination wavelength. The illumination of the skin and the reflected light beams of the first and second image obtained can be guided, as shown in FIG. 6b, by means of a semitransparent mirror through one common objective and through one common optical path. It is also conceivable, however, to position the camera units to the right and to the left of the skin exposure in order to obtain a stereo image with representation of depth. Alternatively, illumination can take place laterally, with the image being obtained centrally, as shown in FIG. 6c. In FIG. 6c, the detection field 94 of the camera unit is arranged centrally, and the illumination is coupled to the skin laterally through the illumination field 95.

The image can be processed by one or more processors or electronic systems, entirely or partially in the camera system 9, in an additional processor system or in the control unit 8.

In addition, it is also possible according to the invention that for an application where a wound with two separated skin parts or an open wound is to be closed, the Laser therapy system additionally comprises a dispenser unit for a skin glue and/or for a plaster (BAND-AID®), which are adapted to be used together with the Laser therapy system and to induce reactions in the skin during light irradiation.

The skin glue preferably consists of a homogeneous mixture of an organic skin glue, such as dihydroxyacetone or DHA, and the Photosensitizer containing agent, such as for instance riboflavin. The skin glue has a first adhesive force for adhering the two separated skin parts together. A first conglutination of the skin and/or of tissue parts is alternatively also conceivable with ionized nano-particles of opposite polarization from a first to a second rim of the wound. The Photosensitizer contained therein induces a reaction in the skin during which through the UVA light spot irradiation a network of collagen and elastin is formed. The Laser therapy system has the characteristics described above of forming the basic collagen and elastin network 25 in a targeted position in the depth of the skin wherein the light spots can be guided in a manual or an automated manner. Additionally, it is also possible to perform a more intensive UVA light treatment with instantaneously forming collagen and elastin so as to achieve a higher tenacity in less time. Further treatment with the second light spots of the second wavelength can take place as described above.

The plaster (BAND-AID®) is of such a kind that it preferably has an isolating protective function against infections; also, it has a high light transparency so as to be transparent for light beams of the first and the second wavelength of the Laser therapy system after the plaster (BAND-AID®) has been placed on the wound. Furthermore, it has flexibility so as to adapt to a skin surface, it has adhesive force so as to stick to the skin and it has a certain tensile strength for adhering the skin parts together. The plaster (BAND-AID®) preferably has nano suction cups on the bottom for producing the adhesive force.

It is also possible for the preferred plaster (BAND-AID®) to have on the bottom a gel layer of another Photosensitizer containing agent which is absorbed by the skin and can then be brought to reaction in or on the skin by the Laser therapy system so as to produce a first protective layer on the skin.

When first hemorrhages have healed, the Laser therapy system can again be used and function as Laser needling by using the second Laser light so as to ensure a further release of the growth factors and in the end complete the process of skin regeneration.

With the Laser therapy system, it is possible to not only induce undifferentiated growth of the exoskeleton but also "physiological" regeneration without scars. In this manner, the skin in its entire function and morphology is not simply "welded together" but regenerated in the sense of a "restitutio ad integrum".

In addition, it is also conceivable according to the invention that the Laser therapy system with its camera system 9 is employed in deeper regions up to 15 mm under the skin, where for instance collagen and elastin are first specifically induced to connect separated vessels or to cover injured vessels by means of UVA light spots, in order to connect or strengthen them, after which, as described above, preferably the second light spots are applied for further strengthening the matrix-shaped collagen and elastin basic structure 25. It is also possible to connect or strengthen, respectively, exposed vessels or tissues in this manner.

Moreover, calibration parameters are kept stored in the Laser therapy system, which parameters can be updated as desired by a calibration dummy.

Furthermore, the Laser therapy system preferably comprises a cooling unit for the skin which comprises either the adapter plate (7) itself or an upstream highly transparent cooling plate.

It is also conceivable that the Laser therapy system is adapted for use on the eye, wherein the skin of the eye, in particular the sclera or the conjunctiva, is treated accordingly. By application on the conjunctiva, the conjunctiva is strengthened and whitened. By application on the sclera, the sclera and the entire eyeball are strengthened so that the eye is shortened along its optical axis and a myopia is corrected.

Description of the Method and Physiology

In a young and healthy skin, there is a natural, web-like collagen structure in the region of the dermis 22, which serves as an exoskeleton for the epidermis 21 above it and extends the latter, so to speak, like a tent. Between the epidermis 21 and the dermis 22, branched, orthogonal elastin fibers and the basic substance (proteoglycanes, glycoaminoglycanes etc.) are located. This physiological anatomic structure provides young skin with its natural elasticity and strength typical for it. With aging, the matrix-like collagen and elastin structure and the elastic exoskeleton slowly dissolve and are replaced by few thickened, non-directional and non-specifically linked, glycosylated collagen fibers.

In case of an injury or a cut reaching down into the dermal skin level, the connective tissue and thus the collagen and elastin structure are discretely interrupted.

A novel treatment method for skin rejuvenation comprises in a first step of treatment the restoration of the lost natural collagen and elastin basic structure and elastin matrix with precise positioning and definition, to such a degree that it is arranged and orientated physiologically and anatomically correct and developed sufficiently to be able to serve as the first basic collagen and elastin framework and as the initial collagen and elastin basic structure 25 for the collagen forming fibroblasts which defines their direction. In this manner, a collagen and elastin basic structure 25 is formed which is similar or identical to the original young collagen and elastin structure, with the physiological characteristics associated with it such as elasticity, strength and morphology.

The first step of treatment preferably comprises the application of the Photosensitizer containing agent which penetrates the skin down to the dermis 22 and contains riboflavin as a cream or gel and which is absorbed into the region of the papillary dermis 22 in approximately 10-30 minutes. After the agent has penetrated the papillary region to sufficient depth, the UVA light spots are targeted between and around the papillae, respectively, with specific energies so that at the respective UVA light spots, collagen and elastin fibers are cross-linked according to the lysyl oxidase reaction. In other words, the Photosensitizer containing agent catalyzes the collagen and elastin cross-linking in the sense of an aldol condensation, similar to the lysyl oxidase reaction. The next, adjacent UVA light spots are positioned or generated, respectively, close enough to the previous ones so as to restore the lost physiologically natural collagen and elastin basic structure 25 to which further collagen and elastin can be attached. Preferably, the UVA light is produced in pulses as the focused light beam 51 with the UVA light spot or the focus point 52 being guided specifically to the desired site on the papilla. With the pulsed, focused light beam 51, the entry area into the skin is substantially larger than the cross-sectional area in the focus point 52 so that accordingly the light density in the focus point 52 is substantially greater than within the entry area where the light enters the skin. The light intensity and pulse duration of the UVA light in the focus point 52 are set such that collagen and elastin are securely formed in the light spot. With light-pulse generation, a plurality of adjacent light pulses can also be created simultaneously, provided that they are located in a physiologically useful position, in order to reduce the treatment time. Since, unfortunately, UVA light also has a cytotoxic effect, it is used as sparingly as possible so that only a thin collagen and elastin basic structure 25 is created which is sufficient to serve as a directional basic framework for collagen and elastin which are formed later. The energy of the UVA light spot is kept low enough to be completely absorbed by the Photosensitizer and have precise targeted effects, with minimum or no collateral damage. Preferably, the application of the UVA light and positioning of the light spots in the treatment region around the papillae is supported by the imaging unit, for instance by the Optical Coherence Tomography (OCT) by means of which the skin and its treatment area are represented three-dimensionally in depth so that e.g. the papillae 23, the vessels 24, nerves, hair roots, sebaceous glands and the like are represented and the light spots can be set more precisely. With a simpler preferred treatment device or a Laser therapy system without integrated imaging unit, the light spot matrix is created with a predefined grid in the depth of the skin after the respective skin type has been defined. A further preferred treatment device measures, by means of a simpler, reflection-photometric or diascopic method, only the depth and position of the papillary layer without representing the skin in detail, in order to generate the light spot matrix in the correct, defined depth and at the correct positions. In alternative to OCT, the fluorescence microscopy or fluorescence tomography imaging method can be employed for obtaining an image of structures within the skin, such as the papillae, arterioles, collagen fibers or parts thereof, for activating the respective light spots.

In the second treatment step, the formation of further collagen and elastin growing into the collagen and elastin basic structure 25 and causing cross-linking is induced by Laser light. For this purpose either Laser needling or a less light intensive punctuation is applied, such that the end arterioles of the papillary dermis as the target region for the treatment of the skin will become permeable for blood cells as for instance the thrombocytes. Herewith growth factors and Cytokines get set free which activates fibroblasts. By the activation of the fibroblasts a further built-up of collagen and elastin along the before created collagen and elastin basic structure 25 takes place. For this purpose, preferably the pulsed second light source 3 is used by means of which preferably greater energies can be released in the light spot than with UVA light treatment. Here as well, light beams 51 focused by lenses are used which enter the skin with the first cross-sectional area and the first light density and which have a substantially smaller cross-sectional area and a substantially greater light density in the focus point in the depth of the skin than at the entry point of the skin. The focal length, the light intensity and the pulse duration are such that the light spot is in the correct depth of the skin, that the energy released there is great enough for therapeutic application and that the skin surface is not perforated or damaged as little as possible, respectively. With this method as well, support by the OCT unit or by another alternative imaging unit is an advantage for positioning and generating the second light spots in the correct depth of the skin at the respective end arterioles. Other imaging methods are conceivable as well.

Another novel treatment method represents an improvement of wound closure and would healing. In a first step of treatment, first the skin parts are properly connected, the wound is closed, and then the initial collagen and elastin basic structure 25 is formed by targeted UVA light spots and related collagen/elastin cross-linking. Preferably, for strengthening the wound closure, also a highly transparent plaster (BAND-AID®) can be applied on the wound which is sufficiently transparent for the UVA and the second light spots. It is conceivable for the plaster (BAND-AID®) to also contain additional medicinal components which promote the healing process. Instead of or in addition to the highly transparent plaster (BAND-AID®), the use of an organic skin glue, such as dihydroxyacetone or DHA, is possible, which is mixed with riboflavin to form a homogeneous mixture for adhering the skin parts to each other. Similar to what is mentioned above, the skin structure is represented by means of OCT, and the UVA light spots are applied in a targeted manner for cross-linking one skin part with the other as the collagen and elastin basic structure 25. The created bridges between one skin part and the other cause an orientation and integration of additional collagen and elastin. By a later, additional Laser needling with the second wavelength, after the first hemorrhage has subsided, other sites of microbleeding on the bottom or the rim of the wound can be created, thus inducing the release of additional growth factors.

The generation of e.g. organ skeletons or basic structures of other tissues in the sense of tissue engineering from, for instance, collagen which has been created in a recombinant manner, is conceivable as well. For this purpose, e.g. by means of a high-resolution Optical Coherence Tomography (OCT) or a different imaging method, tissue is scanned and then accordingly treated with light spots suitable for the specific tissue in order to create the corresponding collagen cross-links. It is also conceivable to reconnect discontinuous tissue structures, such as severed vessels, peripheral or central nerves, in this manner.

Together with the Laser therapy system according to one or more of the following Claims, the novel method for skin treatment is introduced, wherein in the first step the Photosensitizer containing agent is applied on the skin. After its main penetration of, above all, the UVA light spots of the first wavelength are precisely generated adjacent to each other and along web-like paths at the sites of the papillary dermis between and around the papillae 23, in which manner the collagen and elastin basic structure is formed instantaneously in the papillary skin region. The UVA light spots are generated and applied into the skin such that the light density in entry into the skin with the first cross-sectional area is substantially lower than in the light spot so that the epidermis is affected less and, above all, not perforated.

In the second step, the second light spots with the second wavelength are created in the papillae of the treatment region in a targeted manner. During this process, the focal length of the focused light beam 51, the pulse pause time and the energy are set in such a way that through the light spot in the papilla 23, the end arterioles become permeable for the corpuscular blood cells. The second light spots are generated and applied into the skin such that the light density in entry into the skin with the first cross-sectional area is substantially lower than in the light spot so that the epidermis is affected less and, above all, not perforated.

Other possible embodiments are described in the following Claims. Moreover, while an exemplary and preferred embodiment has been described, those having skill in the art will recognize various changes, modifications, additions and applications other than those expressly identified. Such changes, additions, modifications and additional applications are within the scope of the present invention.

LIST OF REFERENCE NUMBERS

1 Dispense unit for dispensing an agent
10 monitor
10a first representation
10b second representation
100-103 positions
104 light source unit
2 UVA light source, or first light source
21 epidermis
22 dermis
23 papilla
24 blood vessels
25 collagen an elastin basic structure
26 additional collagen
3 second light source, or Laser light source
4 optical system
5 optical deflection and focusing system
51 focused light beam
52 focus point (of the focused light beam)
53 first lens system (for light-beam expansion)
54 second lens system (for light-beam focusing)
55 lens
56 light conductor
57 optical fiber beam
58 light adapter head
6 electromechanical adjusting device
7 adapter plate
8 control unit
81 navigation control device
9 camera system
91 camera unit (e. g. CCD sensor)
92 illumination source
93 optical filter
94 detection field
95 illumination field
96-98 absorption coefficient characteristic curves

The invention claimed is:

1. A laser therapy system for skin treatment in a volume-like treatment region in a depth of the skin, comprising:
   a) a photosensitizer-containing agent;
   b) a dispenser for applying the photosensitizer-containing agent on the skin;
   c) a first light source which generates at least one first light with a first wavelength in the ultraviolet A (UVA) range to mediate formation of collagen and elastin cross-linking in the treatment region in the presence of the photosensitizer containing agent when focused in the treatment region;
   d) a second light source including an infrared (IR) laser light source which generates at least one second light with a second wavelength to increase permeability of blood corpuscles in end arterioles in the treatment region;
   e) an optical system in communication with the first and the second light source and with which the at least one first and second light is taken up and focused in the treatment volume comprising an optical deflection and focusing system comprising an adapter plate said optical system is configured to deflect and focus through said adapter plate said first light to first focus points and said second light to second focus points into the treatment region, said first focus points are focused between and around respective papillae in said skin, said second focus points are focused at end arterioles within the respective papillae in said skin;
   f) an imaging system, said imaging system comprising means for recognizing said papillae and areas between the papillae and generating image data; and
   g) a control unit comprising a processor unit configured to receive image data from the said imaging system, to compute and assign xyz positions for the first focus points between and around papillae in said skin and the second focus points on end arterioles, and to control the optical system, the first light source and the second light source, such that said first focus points are focused between and around the papillae and said second focus points are focused at the end arterioles within the papillae.

2. The laser therapy system according to claim 1, wherein said imaging system comprising an imaging unit with a camera system and a monitor,
   the camera system including a camera in communication with said optical system and includes a detection field (94) which, by means of an optical path of said optical system, covers the treatment region behind said adapter plate;
   wherein an image of the treatment region with x/y/z coordinates represented on the monitor (10) correlates with x/y/z coordinates of said optical system, the control unit and said focus points, and by means of a navigation cross hair on the image, a light spot is created in the treatment region at precisely the displayed site, and/or
   wherein said control unit takes into account, during calculation of the x/y/z coordinates of the respective focus point in the treatment region behind an adapter plate, light refraction of the skin and any additional foil or a plaster between the adapter plate and the skin.

3. The laser therapy system according to claim 2, wherein the camera system comprises an Optical Coherence Tomography (OCT) adapted to provide a three-dimensional representation of the treatment region of the skin and to make visible collagen fibers, elastin, hair roots, papillae, arterioles, end arterioles, treated skin tissue, yet untreated skin tissue or combinations thereof.

4. The laser therapy system according to claim 2, wherein the processor of the laser therapy system recognizes, by a second continuous pattern recognition in the image of the treatment region behind the adapter plate, a possible displacement of the adapter plate on the skin and recognizes in addition which region of the treatment region has already been treated so as to then treat only the region of the treatment region further which is still untreated, wherein the treated region and the untreated region of the treatment region is represented in different colors on the monitor.

5. The laser therapy system according to claim 1, wherein the photosensitizer containing agent is a cream or a gel with the effect of penetrating the skin and supporting the formation of collagen and elastin, and contains riboflavin (vitamin B2) and coenzymes for synthesis of collagen and elastin, namely vitamin A, vitamin E and/or vitamin C, and/or
   wherein said dispenser is a tube, a tin, a dosing unit, a gel plaster or an applicator with a disposable syringe, and/or
   wherein said laser therapy system additionally has an alarm timer indicating that the agent has been sufficiently absorbed into the skin.

6. The laser therapy system according to claim 1, wherein the first light source comprises at least one UVA laser or a UVA lamp with the first wavelength within the range of 340-450 nm.

7. The laser therapy system according to claim 1, said second light source comprises at least one IR laser, said second wavelength is within a range of 800-2000 nm.

8. The laser therapy system according to claim 1, said second light source further comprising a laser or a plurality of laser diodes with light whose wavelength is in a range of 450-550 nm or 550-650 nm or of 650-800 nm and being selected such that it is absorbed more by hemoglobin than by remaining tissue of the skin.

9. The laser therapy system according to claim 1, the first and/or the second light source comprises several individual light sources arranged with a specific spacing configured to generate several first and/or second light beams simultaneously to form a beam matrix, to be focused at different sites of the treatment region.

10. The laser therapy system according to claim 1, said optical system comprises an object selected from the group consisting of at least one lens, one concave lens, one cylindrical lens, one diffuser lens, one Fresnel lens, one liquid lens, one first lens system, one second lens system, one light conductor, one fiber-optic light guide, one light adapter or a combination thereof, and/or
wherein the cross-sectional area in the focus point is smaller by a multiple of the cross-sectional area of the light entry into the skin, the multiple being 3-1000.

11. The laser therapy system according to claim 1, said optical system comprises a plurality of optical deflection and focusing systems arranged therein adapted to generate a corresponding plurality of focused light-beams and focus points with corresponding light spots behind said adapter plate in a treatment region of said skin.

12. The laser therapy system according to claim 1, wherein the focus points of the focused light of the first wavelength correspond to the focus points of the focused light of the second wavelength, with the exception of deviations due to different refractive indices with the different wavelengths, or wherein the focus points of the focused light of the first wavelength are offset from the focus points of the focused light of the second wavelength by a defined offset.

13. The laser therapy system according to claim 1, further comprising electromechanical adjustment device comprises actuators which are connected, for the purpose of light deflection and/or shifting of the focus point, with reflecting mirrors, semitransparent mirrors, with lens systems, shutters, shifting elements, light guides, optical filters or combinations thereof, so as to be able to position the respective focus points in the treatment region in a x/y/z direction in a targeted manner.

14. The laser therapy system according to claim 1, wherein said control unit generates light spots with the first and/or the second wavelength behind said adapter plate in a treatment region of said skin in an automated manner along a predefined or previously determined light spot matrix, the light spots being either created by at least two light spots at a time simultaneously or by a sequence of individual light spots.

15. The laser therapy system according to claim 1, wherein calibration parameters of said laser therapy system are stored in said processor and/or wherein before treatment, the laser therapy system is calibrated by means of a calibration dummy.

16. The laser therapy system according to claim 1, wherein the adapter plate is transparent and adapted to be part of a cooling unit to be applied directly on the skin above the treatment region below it.

17. The laser therapy system according to claim 1, wherein the dispenser contains a skin-glue and/or with a plaster, wherein the skin-glue consists of a mixture of an organic skin-glue and the photosensitizer containing agent and wherein the plaster consists of a material which is transparent for the first wavelength and/or for the second wavelength and which at the bottom has an adherent effect on the skin.

18. The laser therapy system according to claim 1, wherein said second light source produces light-pulse duration of between 10 ps and 100 µs.

19. The laser therapy system according to claim 1, wherein said photosensitizer containing agent is fluorescent for determining the penetration depth into the skin.

20. A method for skin treatment in a volume-like treatment region in a depth of skin using the laser therapy system of claim 1, method comprising:
(a) applying a photosensitizer containing agent on the skin;
(b) recognizing papillae and areas between the papillae and generating image data with an imaging system of claim 1;
(c) using the control unit of claim 1 to receive said image data from said imaging system, and to compute and assign xyz positions for first focus points between and around papillae in said skin and second focus points at end arterioles, such that said first focus points are focused between and around the papillae and said second focus points are focused at the end arterioles within the papillae;
(d) providing a first light source according to claim 1 which generates at least one first light with a first wavelength in the UVA range;
(e) providing a second light source according to claim 1 which generates at least one second light with a second wavelength including an IR laser;
(f) irradiating the skin with said at least one first and second light, said irradiating including focusing said at least one first and second light by an optical system in the treatment region, said optical system comprising an optical deflection and focusing system comprising an adapter plate, said optical system deflects and focuses through said adapter plate said first light to said first focus points and said second light to said second focus points into the treatment region,
said first focus points are focused between and around respective papillae in said skin to mediate formation of collagen and elastin cross-linking in the treatment region in the presence of the photosensitizer containing agent,
said second focus points are focused at said end arterioles within the respective papillae in said skin to increase permeability of blood corpuscles in end arterioles in the treatment region.

21. The method according to claim 20 wherein said imaging system further comprise a camera and a monitor, and wherein said method further comprise visualizing skin structure in said volume-like treatment region and said first and second focus points by said camera and monitor.

* * * * *